United States Patent [19]

Meul

[11] Patent Number: 5,243,070
[45] Date of Patent: Sep. 7, 1993

[54] PROCESS FOR RESOLUTION OF RACEMATES OF 2,2-DIMETHYLCYCLOPROPANECARBOXYLIC ACID

[75] Inventor: Thomas Meul, Visp, Switzerland

[73] Assignee: Lonza Ltd., Gampel/Valais, Switzerland

[21] Appl. No.: 711,018

[22] Filed: Jun. 6, 1991

[30] Foreign Application Priority Data

Jun. 14, 1990 [CH] Switzerland ............ 1999/90

[51] Int. Cl.⁵ .................................... C07B 57/00
[52] U.S. Cl. ...................... 562/401; 560/60; 562/506
[58] Field of Search ............ 562/506, 401; 560/60

[56] References Cited

U.S. PATENT DOCUMENTS

| | | | |
|---|---|---|---|
| 4,198,524 | 4/1980 | Tashiro et al. | 562/470 |
| 4,340,751 | 7/1982 | Nohira et al. | 562/401 |
| 4,345,090 | 8/1982 | Neumann et al. | 560/124 |
| 4,419,524 | 12/1983 | Lindwurm et al. | 562/506 |
| 4,487,956 | 12/1984 | Suzukamo et al. | 560/124 |
| 4,683,089 | 7/1987 | Leigh | 562/401 |
| 4,780,252 | 10/1988 | Leigh | 562/401 |

FOREIGN PATENT DOCUMENTS

| | | |
|---|---|---|
| 0039511 | 11/1981 | European Pat. Off. |
| 0048301 | 3/1982 | European Pat. Off. |
| 60-56936 | 2/1985 | Japan |
| 60-56942 | 2/1985 | Japan |
| 1260847 | 1/1972 | United Kingdom |

Primary Examiner—José G. Dees
Assistant Examiner—Vera C. Clarke
Attorney, Agent, or Firm—Fisher, Christen & Sabol

[57] ABSTRACT

The enantiomers of 2,2-dimethylcyclopropanecarboxylic acid are separated by esterification with the hydroxy group of optically active mandelic acid methyl ester, crystallization of the diastereomeric esters and subsequent hydrolysis of the diastereomeric esters.

21 Claims, No Drawings

PROCESS FOR RESOLUTION OF RACEMATES OF 2,2-DIMETHYLCYCLOPROPANECARBOXYLIC ACID

BACKGROUND OF THE INVENTION

1. Field Of The Invention

The invention relates to the production of optically-pure 2,2-dimethylcyclopropane-carboxylic acid by resolution of its racemates.

2. Background Art 2,2-Dimethylcyclopropanecarboxylic acid is an important intermediate product for the synthesis of enzyme inhibitor cilastatin (European Patent No. 0,048,301) and of insecticides of the pyrethrin type (British Patent No. 1,260,847), respectively.

In particular for the production of pharmaceutical active ingredients, it is desirable to have available 2,2-dimethylcyclopropanecarboxylic acid in optically pure form, i.e., in the form of pure (S)-(+)- or pure (R)-(−)-enantiomers. Since the chemical synthesis of 2,2-dimethylcyclopropanecarboxylic acid provides the compound in the form of its racemate, it is necessary to perform a resolution of this racemate. Such resolutions of racemates are usually brought about in that the enantiomer mixture to be separated first is converted to a mixture of diastereomeric derivatives by an optically active auxiliary substance, which can be separated because of the different physical properties of the diastereomers by fractionating crystallization or chromatography. From the diastereomers thus separated, a pure enantiomer of the compound to be separated and the optically active auxiliary substance is then ideally set free in each case.

In reality, with a given auxiliary substance, even though such substance is optically completely pure, in most cases only the incomplete separation of one pure enantiomer is possible, so that a mixture remains, which mainly consists of the other enantiomer. In less advantageous cases, neither of the two enantiomers can be isolated in pure form. As derivatives of carboxylic acids for the purpose of the resolution of racemates, their salts with optically active bases, in particular amines, are often used. These salts have the advantage that they are formed very easily and quickly and can also be cleaved again by adding a strong acid. For resolution of racemates of 2,2-dimethylcyclopropanecarboxylic acid, (S)-(−)-1-phenylethylamine (British Patent No. 1,260,847), (−)-N-methylephredrine (Japanese Published Patent Application Nos. 60-56936 and 60-56942), quinine (European Published Patent Application No. 0,161,546) and various 1,2-diphenylethylamines (European Published Patent Application No. 0,093,511) have already been used.

With 1-phenylethylamine, neither a satisfactory yield nor a sufficient optical purity was able to be achieved. Quinine yielded an enantiomer in good optical purity, but in poor yield, no yield was indicated for N-methylephedrine. In the case of 1,2-diphenylethylamine, the yield is satisfactory and the optical purity is very good, but the reagent, as also is N-methylephedrine, is very expensive.

Further, it is known that 2,2-dimethylcyclopropanecarboxylic acid can be separated in the enantiomers via the diastereomeric menthyl esters, which are obtainable from the acid chloride with (+)- or (−)-menthol (U.S. Pat. No. 4,487,956). This process does provide usable yields and optical purities, but is relatively complicated in the working-up and requires the use of the relatively expensive menthol.

BROAD DESCRIPTION OF THE INVENTION

The main object of the invention is to provide a process for the resolution of the racemates of 2,2-dimethylcyclopropanecarboxylic acid, which is simple to perform and requires only reasonably priced optically active auxiliary substances which are as nontoxic as possible. Other objects and advantages of the invention are set out herein or are obvious herefrom to one skilled in the art.

According to the invention, the main object of the invention is achieved by the process according to the invention. The invention process involves resolution of the racemates of 2,2-dimethylcyclopropanecarboxylic acid by esterification with an optically active hydroxy compound, followed by the fractionating crystallization of the formed diastereomeric esters and the subsequent hydrolysis of the formed diastereomeric esters. Mandelic acid methyl ester is used as the optically active hydroxy compound.

The fractionating crystallization of the diastereomeric esters is preferably performed with an alkane as a solvent. Preferably n-hexane is used as the alkane. Preferably the esterification of 2,2-dimethylcyclopropanecarboxylic acid by the corresponding racemic acid chloride takes place in the presence of an auxiliary base. Preferably the racemic acid chloride is produced by the reaction of 2,2-dimethylcyclopropanecarboxylic acid with thionyl chloride. Also preferably the racemic acid chloride is produced by using the enantiomer mixture, recovered by hydrolysis from the mother liquor of the crystallization, of 2,2-dimethylcyclopropanecarboxylic acid and is racemized by heating to 100° to 200° C. The hydrolysis of the esters of 2,2-dimethylcyclopropanecarboxylic acid is preferably performed with an aqueous alkali hydroxide. Preferably the 2,2dimethylcyclopropanecarboxylic acid is isolated by acidification and extraction with n-hexane from the hydrolysis mixture.

The invention also includes alpha-(2,2-dimethylcyclopropanecarbonyloxy)-phenylacetic acid methyl ester.

DETAILED DESCRIPTION OF THE INVENTION

It was found surprisingly that optically active mandelic acid methyl ester reacts not only with (RS)-2,2-dimethylcyclopropanecarboxylic acid chloride on the OH group smoothly to the corresponding diastereomeric esters, but that surprisingly the latter are also separable by fractionating crystallization and, after their hydrolysis, the released 2,2-dimethylcyclopropanecarboxylic acid can be separated very easily from the likewise resultant mandelic acid. Mandelic acid, in contrast to 2,2-dimethylcyclopropanecarboxylic acid, is practically insoluble in alkanes and remains in the aqueous phase during the extraction with these alkane solvents.

The process according to the invention is advantageously performed in such a way that the racemic 2,2-dimethylcyclopropanecarboxylic acid is first converted to the corresponding acid chloride. This step is known in the art and can be performed, for example, with thionyl chloride in the presence of catalytic amounts of N,N-dimethylformamide. The acid chloride thus obtained is purified advantageously by distillation. Then, the racemic acid chloride is reacted with optically active mandelic acid methyl ester while adding an auxiliary base to bond the resulting hydrochloric acid. As the auxiliary base, for example, pyridine is used. The esterification is advantageously performed in an inert solvent, such as, dichloromethane.

Of course, it is also within the scope of the invention to perform the esterification by the direct reaction of 2,2dimethylcyclopropanecarboxylic acid with mandelic acid methyl ester in the presence of a catalyst, such as, dicyclohexylcarbodiimide or 1,1'-carbonyldiimidazole. Such esterification methods are known to one skilled in the art and are described, for example, in "Methoden der organischen Chemie", [Methods of Organic Chemistry], (Houben-Weyl), 4th Edition, Vol. E5, p. 659 ff, and Vol. VIII, p. 516 ff.

The diastereomeric esters present after the esterification are fractionatingly crystallized; an alkane is preferably used as the solvent. n-Hexane is especially preferred as the solvent. The diastereomer with the same absolute configuration on both asymmetric centers crystallizes first from n-hexane.

To obtain (S)-(+)-2,2-dimethylcyclopropanecarboxylic acid in optically pure form, (S)-(+)-mandelic acid methyl ester therefore is used advantageously, (R)-ester is correspondingly used for the (R)-acid. An advantage of the process according to the invention lies in the fact that both enantiomers of the mandelic acid and, thus, also their esters are easily accessible.

After the isolation of the desired diastereomeric ester, the latter is hydrolyzed. The hydrolysis is preferably performed according to a usual method with aqueous alkali hydroxide solution, and both ester groups are hydrolyzed in the molecule. Then, by adding a strong acid, for example, hydrochloric acid, 2,2-dimethylcyclopropanecarboxylic acid and mandelic acid, which first are present as anions after the hydrolysis are released. The separation of the optically-pure 2,2-dimethylcyclopropanecarboxylic acid takes place preferably by extraction with a nonpolar solvent. Especially preferred as an extracting agent are the straight-chain, branched or cyclic alkanes having 5 to 10 C atoms. Quite especially preferred is n-hexane, in which mandelic acid is practically insoluble.

The optically-pure 2,2-dimethylcyclopropanecarboxylic acid thus obtained can be further processed in a known way, for example, conversion to the acid chloride and further to th amide.

To use the mother liquor of the crystallization, in which the more easily soluble diastereomer is concentrated, the latter is advantageously also subjected to a hydrolysis.

The enantiomer mixture thus obtained is suitably converted again to the mixture of the acid chlorides, which can be racemized in a way known in the art by heating to 100° to 200° C. The thus obtainable racemic acid chloride can again be added to the initial material of the process according to the invention, so that neither the undesirable enantiomer has to be removed no significant losses occur.

The following examples illustrate the performance of the process according to the invention.

EXAMPLE 1

(RS)-2,2-dimethylcyclopropanecarboxylic acid chloride 52.8 g of (RS)-2,2-dimethylcyclopropanecarboxylic acid and 0.25 g of N,N-dimethylformamide were dissolved in 50 ml of n-hexane and mixed under reflux by instillation with 104.0 g of thionyl chloride in 100 ml of n-hexane. After another 2 hours of stirring under reflux, the solvent was distilled off and the residue was quickly distilled at 200 mbars and 100° C. (bath temperature). The yield of the product was 55.0 g.

EXAMPLE 2

(S,S)-alpha-(2,2-dimethylcyclopropanecarbonnloxy)-phenylacetic acid methyl ester 14.0 g of (S)-2,2-dimethylcyclopropanecarboxylic acid chloride was dissolved in 70 ml of dichloromethane, cooled to 0° C. and mixed as quickly as possible with 8.1 g of pyridine. Then a solution of 17.0 g of (S)-(+)-mandelic acid methyl ester $\{[\alpha]_D^{20} = +146.5°$ (c=1, MeOH)}in 35 ml of dichloromethane was instilled in this mixture at 0° to 5° C. within 10 minutes. The reaction mixture was stirred for another 2 hours at room temperature and then washed in succession with water, dilute hydrochloric acid and again with water. The organic phase was dried on sodium sulfate and concentrated by evaporation. The crude product thus obtained (26.0 g) was suspended in 7.0 ml of n-hexane at room temperature. The crystalline residue was filtered off, dried and recrystallized hot three times from 40 ml of n-hexane, each time. The yield of (S,S)-alpha-2,2-dimethylcyclopropanecarbonyloxy)phenylacetic acid methyl ester was 7.6 g. Other data for the product was:

Melting point: 80° to 82° C., colorless crystals.

$[\alpha]_D^{20}$: +158.0° (c=1, CHCl$_3$).

$^1$H-NMR (300 MHz, C$_6$D$_6$): δ7.43 to 7.52 (m, 2H), 6.97 to 7.12 (m,3H), 6.11 (s, 1H), 3.19 (s,3H), 1.55 to 1.60 (m, 1H), 1.39 (s,3H), 1.19 to 1.23 (m, 1H), 0.86 (s,3H), 0.55 to 0.60 (m, 1H).

EXAMPLE 3

(S)-(+)-2,2-Dimethylcyclopropanecarboxylic acid 18.4 g of (S,S)-alpha-(2,2-dimethylcyclopropanecarbonyloxy)phenylacetic acid methyl ester (produced according to Example 2) was mixed with a solution of 20.6 g of potassium hydroxide (85 percent) in 235 ml of water and stirred for 6 hours at 80° C., and a clear solution was formed. Then the reaction mixture was cooled to room temperature and acidified with dilute hydrochloric acid to pH 1. The aqueous solution was extracted four times with 100 ml of n-hexane, each time. The combined organic phases were dried on sodium sulfate and filtered. After distilling off the solvent, (S)-(+)-2,2-dimethylcyclopropanecarboxylic acid was obtained in a purity (GC) of 99.0 percent. The yield of the product was 7.7 g. Other data for the product was: $[\alpha]_D^{20}$: +146° (neat), corresponding to an optical purity (ee value) greater than or equal to 98 percent.

EXAMPLE 4

Racemization of 2,2-dimethylcyclopropanecarboxylic acid

From the mother liquors resulting during the crystallization of (S,S)-alpha-(2,2-dimethylcyclopropanecarbonyloxy)phenylacetic acid methyl ester according to Example 2, the solvent was distilled off and the residue, analogously to Example 3, was hydrolyzed alkaline and worked up. 11.4 g of 2,2-dimethylcyclopropanecarboxylic acid $\{[\alpha]_D^{20} = -51.8° (c=1, CHCl_3)\}$, consisting of 69 percent of the (R)-(−)- form and 31 percent of the (S)-(+)-form, was obtained. The enantiomer mixture was diluted with 12.0 g of hexane, heated to 75° C. and, within 30 minutes, was mixed by instillation with a mixture of 17.9 g of thionyl chloride and 5.0 g of hexane and refluxed for another 2.5 hours. The solvent and the excess thionyl chloride were distilled off and the residue was heated to 135° C. with stirring for 2 hours. After cooling to room temperature, the acid chloride mixture was hydrolyzed with dilute sodium hydroxide solution, and the resultant aqueous solution was extracted twice with 10 g of toluene, each time. The organic phase was discarded; and the aqueous phase was acidified with concentrated hydrochloric acid and extracted five times with 40 g of hexane, each time. 11.4 g of crude 2,2-dimethylcyclopropanecarboxylic acid, which was distilled in the water jet vacuum, was obtained from the hexane phases by distilling off the solvent. The yield was 9.4 g (83 percent) of colorless, fetid liquid consisting of 48.5 percent of the (S)-(+)-form and 51.5 percent of the (R)-(−)-form.

What is claimed is:

1. Process for resolution of racemates of 2,2-dimethylcyclopropanecarboxylic acid comprising: (a) esterifying the racemates of 2,2-dimethylcyclopropanecarboxylic acid with an optically active hydroxy compound, which is mandelic acid methyl ester, to form diastereomeric esters; (b) fractionating crystallizing the formed diastereomeric esters to separate at least one of the formed diastereomeric esters; and (c) subsequently hydrolyzing at least one of the separated, formed diastereomeric esters, to provide at least one optionally pure enantiomer of 2,2-dimethylcyclopropanecarboxylic acid.

2. The process according to claim 1 wherein the fractionating crystallization of the diastereomeric esters is performed with an alkane as a solvent.

3. The process according to claim 2 wherein the alkane is n-hexane.

4. The process according to claim 3 wherein the hydrolysis of [esters of 2,2-dimethylcyclopropanecarboxylic acid] at least one of the separated, formed diastereomeric esters is performed with an aqueous alkali hydroxide.

5. The process according to claim 4 wherein at least one optionally pure enantiomer of 2,2-dimethylcyclopropanecarboxylic acid from step (c) is isolated by acidification and extraction with n-hexane.

6. The process according to claim 1 wherein the hydrolysis of at least one of the separated formed diastereomeric esters is performed with an aqueous alkali hydroxide.

7. The process according to claim 6 wherein at least one optionally pure enantiomer of 2,2-dimethylcyclopropanecarboxylic acid from step (c) is isolated by acidification and extraction with n-hexane.

8. The process according to claim 1 wherein the esterification is conducted in the presence of a catalyst.

9. The process according to claim 8 wherein the catalyst is dicyclohexylcarbodiimide or 1,1'-carbonyldiimidazole.

10. Process for resolution of racemates of 2,2-dimethylcyclopropanecarboxylic acid comprising: (a) converting the racemates of 2,2-dimethylcyclopropanecarboxylic acid to 2,2-dimethylcyclopropanecarboxylic acid chloride; (b) esterifying the racemates of the 2,2-dimethylcyclopropanecarboxylic acid chloride with an optically active hydroxy compound, which is mandelic acid methyl ester, in the presence of an auxiliary base to form diastereomeric esters; (c) fractionating crystallizing the formed diastereomeric esters to separate at least one of the formed diastereomeric esters, there being left a mother liquor from the fractionating crystallization; and (d) subsequently hydrolyzing at least one of the separated, formed diastereomeric esters, to provide at least one optionally pure enantiomer of 2,2-dimethylcyclopropanecarboxylic acid.

11. The process according to claim 10 wherein the conversion of the racemates of 2,2-dimethylcyclopropanecarboxylic acid is performed with thionyl chloride.

12. The process according to claim 11 wherein the conversion is performed in the presence of a catalytic amount of N,N-dimethylformamide.

13. The process according to claim 10 wherein, between step (a) and step (b), the 2,2-dimethylcyclopropanecarboxylic acid chloride is purified by distillation.

14. The process according to claim 10 wherein the auxiliary base is pyridine.

15. The process according to claim 10 wherein the esterification is performed in an inert solvent.

16. The process according to claim 10 wherein the fractionating crystallization of the diastereomeric esters is performed with an alkane as a solvent.

17. The process according to claim 16 wherein the alkane is n-hexane.

18. The process according to claim 10 wherein hydrolysis of the at least one of the diastereomeric esters is performed with aqueous alkali hydroxide.

19. The process according to claim 10 wherein at least one optically pure enantiomer of 2,2-dimethylcyclopropanecarboxylic acid chloride provided by step (a) is isolated by acidification and extraction with n-hexane and wherein hydrolysis of at least one of the diastereomeric esters is performed with aqueous alkali hydroxide.

20. The process according to claim 10 wherein the mother liquor from step (c) is subjected to hydrolysis, whereby any of the formed diastereomeric esters therein are hydrolyzed to provide a mixture of enantiomers of 2,2-dimethylcyclopropanecarboxylic acid, the mixture of enantiomers of 2,2-dimethylcyclopropanecarboxylic acid is converted to a mixture of enantiomers of 2,2-dimethylcyclopropanecarboxylic acid chloride, the mixture of enantiomers of 2,2-dimethylcyclopropanecarboxylic acid chloride is heated to 100° to 200° C. to provide racemates of 2,2-dimethylcyclopropanecarboxylic acid chloride, and the racemates of 2,2-dimethylcyclopropanecarboxylic acid chloride are recycled to step (b).

21. The process according to claim 20 wherein the hydrolysis of the mother liquor from step (c) is conducted with an alkali hydroxide and the conversion of the mixture of enantiomers of 2,2-dimethylcyclopropanecarboxylic acid is conducted with thionyl chloride.

* * * * *